United States Patent
Seki et al.

(10) Patent No.: US 10,780,133 B2
(45) Date of Patent: Sep. 22, 2020

(54) METHOD FOR PROTECTING LIVER AND A LIVER PROTECTING AGENT

(71) Applicants: THE REGENTS OF THE UNIVERSITY OF CALIFORNIA, Oakland, CA (US); NIPPON ZOKI PHARMACEUTICAL CO., LTD., Osaka (JP)

(72) Inventors: Ekihiro Seki, San Diego, CA (US); Koichi Masuda, San Diego, CA (US); Mitsuru Naiki, Hyogo (JP)

(73) Assignees: NIPPON ZOKI PHARMACEUTICALS CO., LTD., Osaka (JP); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 474 days.

(21) Appl. No.: 15/502,358

(22) PCT Filed: Aug. 7, 2015

(86) PCT No.: PCT/US2015/044204
§ 371 (c)(1),
(2) Date: Feb. 7, 2017

(87) PCT Pub. No.: WO2016/022917
PCT Pub. Date: Feb. 11, 2016

(65) Prior Publication Data
US 2017/0224738 A1    Aug. 10, 2017

Related U.S. Application Data

(60) Provisional application No. 62/035,191, filed on Aug. 8, 2014.

(51) Int. Cl.
| | |
|---|---|
| *A61K 35/36* | (2015.01) |
| *A61K 9/00* | (2006.01) |
| *A61K 35/76* | (2015.01) |
| *C12N 7/00* | (2006.01) |
| *A61K 39/00* | (2006.01) |

(52) U.S. Cl.
CPC ............ *A61K 35/36* (2013.01); *A61K 9/0019* (2013.01); *A61K 9/0053* (2013.01); *A61K 35/76* (2013.01); *C12N 7/00* (2013.01); *A61K 2039/515* (2013.01); *A61K 2039/58* (2013.01); *C12N 2710/24133* (2013.01)

(58) Field of Classification Search
None
See application file for complete search history.

(56) References Cited

U.S. PATENT DOCUMENTS 4,985,254 A    1/1991    Konishi

FOREIGN PATENT DOCUMENTS

| JP | 55/87724 | 7/1980 |
| JP | 3818657 | 9/2006 |
| JP | 4883798 | 2/2012 |

OTHER PUBLICATIONS

Sunami (Hepatology (2012), vol. 56, No. 3, pp. 1117-1128).*
Ishii et al, "Suppression of Experimental Hepatic Cirrhosis and Hepatic Malignant Tumor Development by a Vasoactive Drug," Kanzo, vol. 24, No. 10, pp. 55-60 (1983) and English translation thereof.
Sekiguchi et al., "Immunization with a recombinant vaccinia virus that encodes nonstructural proteins of the Hepatitis C virus suppresses viral protein levels in mouse liver", PLoS One, vol. 7, No. 12, DOI:10.1371/journal.pone.0051656, Dec. 17, 2012, pp. 1-12, abstract p. 2, paragraphs 3, 6, 8, p. 9, paragraphs 6, 8, figure 1.
Krizhanovsky et al., "Senescence of activated stellate cells limits liver fibrosis", Cell., vol. 134, No. 4, DOI: 10.1016/j.cell.2008.06.049, Aug. 22, 2008, pp. 657-667; abstract, p. 665, paragraph 7.
Gilot et al., "Liver protection from apoptosis requires both blockage of initator caspase activities and inhibition of ASK1/JNK pathway via glutathione S-transferase regulation", J Biol Chem., vol. 277, No. 51, DOI: 10.1074/jbc.M207325200, Dec. 20, 2002, pp. 49220-49229, abstract, p. 49221, paragraph 4.
Luedde et al., "NF-kB in the liver-linking injury, fibrosis and hepatocellular carcinoma", Nat Rev Gastroenterol Hepatol, vol. 8, No. 2, DOI: 10.1038/nrgastro.2010.213, Feb. 2011, pp. 1-23, abstract; p. 1, paragraph 2, p. 2, paragraph 4.
Written Opinion (PCT/ISA/237) in PCT/US2015/044204 dated Feb. 2, 2016.

* cited by examiner

*Primary Examiner* — Susan Hoffman
(74) *Attorney, Agent, or Firm* — Greenblum & Bernstein, P.L.C.

(57) ABSTRACT

An object of the present invention is to provide a protective method for liver comprising the administration of an extract from inflamed tissues inoculated with vaccinia virus to a patient who needs the treatment and to provide a liver protective agent, etc. where such an extract is an active ingredient. In the present invention, it has been recognized that, in hepatocytes, activation of NF-B, expression of NF-B target genes, activation of JNK, apoptosis and fat accumulation can be inhibited or suppressed. The agent containing the extract as an active ingredient is a drug exhibiting less adverse action and high safety. Accordingly, the present invention provides very useful protective method for liver and liver protecting agent.

21 Claims, 6 Drawing Sheets

METHOD FOR PROTECTING LIVER AND A LIVER PROTECTING AGENT

CROSS-REFERENCE TO RELATED APPLICATIONS

The present application claims the benefit of U.S. Provisional Patent Application No. 62/035,191 filed Aug. 8, 2014, the disclosure of which is expressly incorporated by reference herein in its entirety.

STATEMENT OF JOINT RESEARCH AGREEMENT

The subject matter disclosed herein was developed and the claimed invention was made by, or on behalf of, The Regents of the University of California and Nippon Zoki Pharmaceutical Co., Ltd., parties to a joint research agreement that was in effect on or before the effective filing date of the claimed invention; and the claimed invention was made as a result of activities undertaken within the scope of the joint research agreement.

TECHNICAL FIELD

The present invention relates to a novel pharmaceutical use of an extract from inflamed tissues inoculated with vaccinia virus (hereinafter, it may also be referred to as "the present extract") or to a novel therapeutic method by the present extract. More particularly, it relates to a method for the protection of liver by, in the liver, inhibition of nuclear factor-κB (NF-κB) activation, by suppression of expression of NF-κB target genes, by inhibition of c-jun N terminal kinase (JNK) activation, by suppression of hepatocyte apoptosis, by suppressing caspase activation and/or by suppression of fat accumulation using the present extract or relates to a liver protecting agent in which the present extract is an active ingredient.

BACKGROUND ART

Chronic liver disease is a common cause of death in the world. Chronic liver diseases include chronic hepatitis B and C, drug-induced hepatitis, alcoholic liver disease and autoimmune hepatitis.

In liver inflammation, an excessive production of inflammatory cytokines, such as interleukin-1β (IL-1β) and tumor necrosis factor α (TNF-α), is observed. IL-1β binding to the IL-1 receptor induces the activation of c-Jun-NH2-terminal kinase (JNK). As a result of JNK activation, AP-1, a transcription factor, is activated, which induces inflammatory response. In parallel, an inhibitor of κB (IκB), a suppressor of a transcription factor NF-κB, is degraded and NF-κB comprising the subunits p65 and p50 is activated. As a result, transcription of inflammatory genes, such as interleukin-6 (IL-6) and nitrogen oxide synthetase 2 (NOS2) is induced in hepatocytes. On the other hand, TNF-α binds to a trimerized TNF receptor, thereby activating JNK and NF-κB. Caspase is a group of cysteine protease that activate the signals causing apoptosis. It is known that hepatocyte apoptosis is mediated by JNK activation via TNF-α in addition to a caspase-dependent apoptosis pathway.

Fatty liver is a preliminary disease of subsequent hepatitis. In fatty liver, excessive amounts of lipid mainly comprising neutral fat are accumulated in hepatocytes. The causes of fatty liver are varied, including overnutrition, obesity, excessive ingestion of alcohol, diabetes, hyperalimentation, some pharmaceutical agents, malnutrition and pregnancy. Even in persons without drinking alcohol, may progress from simple fatty liver to hepatitis, referred to as nonalcoholic steatohepatitis (NASH). It has been reported that 30 to 40% of the population in the United States and, even in Japan, 14% of the population have nonalcoholic fatty liver disease and that 10 to 20% of them progress to NASH. NASH is a progressive liver disease and has a risk of becoming liver cirrhosis, hepatic insufficiency and liver cancer. At present, more than 15% of patients who received liver transplantation had liver cirrhosis related to NASH. In the United States, it is expected that NASH would become the first indication for liver transfection around 2020. Recently, it is suggested that IL-1β and TNF-α participate in the accumulation of fat in the liver.

Interferons are the drug that is currently used for the treatment for liver diseases, mainly for viral hepatitis. Although interferons can reduce the burden of hepatitis virus, it is not always effective to all patients with viral hepatitis and the cost for the treatment is extremely high. In addition, many adverse effects, such as mental disturbance, thrombocytopenia and leucocytopenia, rebound after discontinuance of drug administration and interstitial pneumonia have been reported. To improve liver function, glycyrrhizins and Chinese herbal medicines are also used but in many cases there are no significant therapeutic effects. Therefore, it is required to develop liver protective methods or agents with less adverse effects to treat liver diseases or prevent the progress from fatty liver to liver diseases.

The present inventors have found that the present extract has a protective action for liver by inhibition of NF-κB activation, by suppression of expression of NF-κB target genes, by inhibition of JNK activation, by suppression of hepatocyte apoptosis, by suppression of caspase activation and/or by suppression of accumulation of fat, etc. With regard to the action of the present extract to liver, a protective effect for the production of liver cirrhosis induced by carbon tetrachloride and of malignant liver tumors induced by 3'-methyl-diethylaminoazobenzene was disclosed in Patent Document 1 and non-Patent Document 1. However, there is no disclosure at all therein for the fact that the present extract exhibits inhibition of NF-κB activation, etc. or suppression of apoptosis and a suppressive action for accumulation of fat in liver.

PRIOR ART DOCUMENTS

Patent Document

[Patent Document 1] Japanese Patent Laid-Open No. 55/87724 (pages 5 and 6)

Non-Patent Document

[Non-Patent Document 1] *Kanzo*, vol. 24, no. 10, pages 55 to 60 (1983)

SUMMARY OF THE INVENTION

Problems to be Solved by the Invention

The present invention is to provide a method for the protection of liver comprising the administration of the present extract to patients who need the treatment and also a liver protecting agent, etc. containing the present extract as an active ingredient.

MODE FOR CARRYING OUT THE INVENTION

The present extract is an extract containing a non-proteinous active substance extracted and separated from the inflamed skins of rabbits by the inoculation of vaccinia virus. Although the present extract is liquid in an extracted state, it is also possible to make into a solid by means of drying. A preparation containing the present extract as an active ingredient is very useful as a drug. Since the present extract is an active ingredient of the present preparation in that case, the present extract is a drug substance of the present preparation. In a specific product as the present preparation which is manufactured and distributed by the applicant, there is "a preparation containing an extract from inflamed skins of rabbits inoculated with vaccinia virus" (trade name: NEUROTROPIN [registered trade mark]. In this preparation, there are injection and tablet and both belong to an ethical drug.

Indications of NEUROTROPIN injection are "low back pain, cervicobrachial syndrome, symptomatic neuralgia, itchiness accompanied by skin diseases (eczema, dermatitis, urticaria), allergic rhinitis and sequelae of subacute myelo-optico-neuropathy (SMON) such as coldness, paresthesia and pain". Indications of NEUROTROPIN tablet are "postherpetic neuralgia, low back pain, cervicobrachial syndrome, periarthritis scapulohumeralis and osteoarthritis". NTP preparation has been created and developed as a drug by the applicant. NTP preparation has been appreciated for its excellent advantage for efficacy and safety, sold for many years and established a firm position in the Japanese pharmaceutical market.

The extract from inflamed tissues inoculated with vaccinia virus of the present invention can be obtained by the following manner: inflamed tissues inflamed by the inoculation with vaccinia virus is crushed; an extraction solvent is added; the tissue fragments are removed therefrom; then deproteinization is carried out; the deproteinized solution is adsorbed onto an adsorbent; and then the active ingredient is eluted. For example, the present extract can be prepared by such a manner that inflamed skins of rabbits by the inoculation of vaccinia virus are collected, crushed and processed by adding an extraction solvent thereto, tissue fragments are removed therefrom, a treatment for removal of protein (deproteinization) is carried out, the resulting one is adsorbed with an adsorbent under an acidic condition and then an active ingredient is eluted under a basic condition therefrom.

As for animals in order to obtain the inflamed tissues by the inoculation of vaccinia virus, various animals that is infected with vaccinia virus such as rabbits, cows, horses, sheep, goats, monkeys, rats or mice can be used, and preferred inflamed tissues are inflamed skins of rabbits.

With regard to a rabbit, any rabbit may be used so far as it belongs to *Lagomorpha*. Examples thereof include *Oryctolagus cuniculus*, domestic rabbit (domesticated *Oryctolagus cuniculus*), hare (Japanese hare), mouse hare and snowshoe hare. Among them, it is appropriate to use domestic rabbit. In Japan, there is family rabbit called "Kato" which has been bred since old time and frequently used as livestock or experimental animal and it is another name of domestic rabbit. There are many breeds in domestic rabbit and the breeds being called Japanese white and New Zealand white are advantageously used.

Vaccinia virus used herein may be in any strain. Examples thereof include Lister strain, Dairen strain, Ikeda strain, EM-63 strain and New York City Board of Health strain.

As to basic extracting steps for the present extract, the following steps are used for example.

About (A):

The inflamed skins of rabbits by the intradermal inoculation of vaccinia virus are collected. The collected skins are washed and disinfected using a phenol solution, etc. This inflamed skins are crushed and an extraction solvent in 1- to 5-fold thereof by volume is added thereto. Here, the term "crush" means to finely break down into minces using a mincing machine or the like. As to the extraction solvent, there may be used distilled water, physiological saline, weakly acidic to weakly basic buffer, etc. and bactericidal/antiseptic agent such as phenol, stabilizer such as glycerin, salts such as sodium chloride, potassium chloride or magnesium chloride, etc. may be appropriately added thereto. At that time, it is also possible that the cell tissue is destroyed by a treatment such as freezing/melting, ultrasonic wave, cell membrane dissolving enzyme or surfactant so as to make the extraction easier. The resulting suspension is allowed to stand for 5 to 12 days. During that period, the suspension may be heated at 30 to 45° C. with or without appropriate stirring. The resulting liquid is filtered or centrifuged to remove the tissue fragments whereupon a crude extract (filtrate or supernatant) is obtained.

About (B)

The crude extract obtained in (A) is subjected to a deproteinizing treatment. The deproteinization may be carried out by a known method which has been usually conducted and a method such as heating treatment, treatment with a protein denaturant (such as acid, base, urea, guanidine or an organic solvent including acetone), isoelectric precipitation or salting-out may be applied. After that, a common method for the removal of insoluble matters such as filtration using filter paper (such as cellulose or nitrocellulose), glass filter, Celite or Seitz filter, ultrafiltration or centrifugation is conducted to give a filtrate or a supernatant wherefrom the separated insoluble protein is removed.

About (C)

The filtrate or supernatant obtained in (B) is adjusted to acidic or, preferably, to pH 3.5 to 5.5 to conduct an operation of adsorbing with an adsorbent. Examples of the usable adsorbent include activated carbon and kaolin. An adsorbent is added to the extract followed by stirring or the extract is passed through a column filled with an adsorbent so that the active ingredient can be adsorbed with the adsorbent. When an adsorbent is added to the extract, the adsorbent with which the active ingredient is adsorbed can be obtained by means of filtration, centrifugation, etc. to remove the solution.

About (D)

For elution (desorption) of the active ingredient from the adsorbent obtained in (C), an elution solvent is added to said adsorbent and adjusted to basic or, preferably, to pH 9 to 12, elution is conducted at room temperature or with suitable heating, or with stirring, and then the adsorbent is removed by a common method such as filtration or centrifugation. As to the extraction solvent used therefore, there may be used a basic solvent such as water, methanol, ethanol, isopropanol or the like adjusted to basic pH or an appropriate mixed solvent thereof and preferably, water adjusted to pH 9 to 12 may be used. Amount of the extracting solvent may be appropriately set. In order to use the eluate obtained as such as a drug substance, the pH is appropriately adjusted to nearly neutral or the like whereby an extract from inflamed skins of rabbits inoculated with vaccinia virus (the present extract) can be finally obtained.

Since the present extract is liquid at the stage of being prepared, it is also possible that said extract is appropriately concentrated or diluted to make into a desired concentration. When a preparation is manufactured from the present extract, it is preferred to apply a sterilizing treatment with heating. For making into an injection preparation, it is possible to add sodium chloride or the like so as to prepare a solution being isotonic to physiological saline. It is also possible that the present extract in a liquid state is subjected to an appropriate operation such as concentration to dryness whereby a solid preparation for oral administration such as tablet is manufactured. Specific methods for the manufacture of solid preparation for oral administration from the present extract are disclosed in the specifications of Japanese Patent Nos. 3,818,657 and 4,883,798. The present preparation includes an injection preparation, a solid preparation for oral administration, etc. prepared as such.

Examples of an administration method of a pharmaceutically effective amount of an extract from inflamed tissues inoculated with vaccinia virus to a patient who needs a treatment include oral and other administrations such as subcutaneous, intramuscular and intravenous administrations. The dose can be suitably determined depending on the type of extract from inflamed tissues inoculated with vaccinia virus. The dose that is approved in the commercially available preparation according to the "Drugs in Japan, Ethical Drugs" (page 2978) is principally 16 NU per day by oral administration and 3.6 to 7.2 NU per day by injection. However, the dose may be appropriately increased or decreased depending on the type of disease, degree of seriousness, individual difference in the patients, method of administration, period of administration and the like (NU: Neurotropin unit. Neurotropin unit is defined by ED50 value of analgesic effect measured by a modified Randall-Selitto method using SART-stressed mice that are chronic stressed animals showing a lowered pain threshold than normal animals. One NU indicates the activity of 1 mg of analgesic ingredients in Neurotropin preparations when the ED50 value is 100 mg/kg of the preparation).

Hereinafter, there will be shown examples of the method for the manufacture of the present extract and also results of pharmacological tests concerning the protective action of liver by novel pharmacological action of the present extract such as inhibition of NF-κB activation, suppression of expression of NF-κB target genes, inhibition of JNK activation, suppression of hepatocyte apoptosis, inhibition of caspase activation and suppression of fat accumulation although the present invention shall be never restricted by the description of those Examples.

EXAMPLES

Example 1 (Manufacture of the Present Extract)

Skins of healthy adult rabbits were inoculated with vaccinia virus intradermally and the inflamed skins were cut and collected. The collected skins were washed and disinfected by a phenol solution, an excessive phenol solution was removed and the residue was crushed. A phenol solution was added thereto and mixed therewith and the mixture was allowed to stand for 3 to 7 days, and further heated at 35 to 40° C. together with stirring for 3 to 4 days. After that, an extracted solution obtained by a solid-liquid separation was adjusted to pH 4.5 to 5.2 with hydrochloric acid, heated at 90 to 100° C. for 30 minutes and filtered to remove protein. The filtrate was adjusted to pH 9.0 to 9.5 with sodium hydroxide, heated at 90 to 100° C. for 15 minutes and subjected to a solid-liquid separation.

The resulting deproteinized solution was adjusted to pH 4.0 to 4.3 with hydrochloric acid, activated carbon in an amount of 2% to the mass of the deproteinized solution was added thereto and the mixture was stirred for 2 hours and subjected to the solid-liquid separation. Water was added to the collected activated carbon followed by adjusting to pH 9.5 to 10 with sodium hydroxide and the mixture was stirred at 60° C. for 90 to 100 minutes and centrifuged to give a supernatant. Water was added again to the activated carbon precipitated upon the centrifugation followed by adjusting to pH 10.5 to 11 with sodium hydroxide and the mixture was stirred at 60° C. for 90 to 100 minutes and centrifuged to give a supernatant. Both supernatants were combined and neutralized with hydrochloric acid to give the present extract.

Example 2 (Test Method)

Now there will be shown an example of pharmacological tests showing the action activity of the inhibition of NF-κB activation in hepatocytes, the inhibition of JNK activation, the suppression of expression of NF-κB target genes, the suppression of caspase activation, the suppression of apoptosis and the suppression of fat accumulation using the present extract prepared in the above Example 1 as a test drug.

1) Mice, Reagents and Cells

Wild-type C57BL/6 mice were purchased from the Jackson Laboratory (Bar Harbor). The NF-κB reporter transgenic mice used in this study express green fluorescent protein (GFP) under control of the NF-κB promoter. Primary culture hepatocytes were isolated from wild-type C57BL/6 mice and NF-κB reporter GFP transgenic mice by the in situ collagenase perfusion method. Cells with 90% or more survival rate were used for the experiments. After two hours from the incubation of hepatocytes, M199 medium containing 10% FBS was changed to serum-free M199 media or 1% FBS M199 media for overnight culture. After that, the following treatment was carried out. Throughout the experiment, M199 medium was used for the incubation of hepatocytes.

2) Measurement of NF-κB Activity by the GFP Reporter

After overnight serum starvation, primary culture hepatocytes isolated from NF-κB reporter GFP transgenic mice were first treated with NTP (0, 0.01, 0.1, 0.2 or 0.4 NU/mL) for 1, 6 or 24 hour(s). The cells were then treated in the presence or the absence of 10 ng/mL recombinant IL-1β (R&D Systems) for 6 hours. The fluorescent signal intensity of GFP of hepatocytes was then measured under a fluorescence microscope. As to data, the measurement was done for 3 wells each and mean value and standard error were determined.

3) Measurement of Activity of NF-κB by NF-κB Luciferase Assay

After changing the media to 1% FBS M199, wild type primary culture hepatocytes or hepatic stellate cells were infected with adenoviral NF-κB-luciferase reporter at moi (multiplicity of infection) 10 for 16 hours. The cells were first treated with the present extract (0.2 NU/mL) for 1 hour before stimulation with 2 ng/mL IL-1β, 2 ng/mL TNF-α (R&D Systems) or 10 ng/mL lipopolysaccharide (LPS). Luciferase assay was conducted after 8 hours of the treatment with IL-1β, TNF-α or LPS. Luciferase activity was normalized to the protein concentration of hepatocytes in each well. As to data, the measurement was done for 3 wells each and mean value and standard error were determined.

4) Quantitative Real-Time PCR

Primary culture hepatocytes were first treated with the present extract (0.2 NU/mL) for one hour prior to stimulation with IL-1β or TNF-α. Two or six hours after the stimulation with IL-1β or TNF-α, an extraction of total RNA using TRIZOL (Life Technologies) was followed by subjecting to reverse transcription of total RNA to cDNA. The cDNA subsequently underwent quantitative real-time PCR using the CFX96 real-time PCR system (Bio-Rad). As to data, the measurement was done for 3 wells each and mean value and standard error were determined.

5) Western Blot

Protein extracts were electrophoresed, blotted, and then made to react with antibodies for IκBα, phosphorylated p65, p65, phosphorylated JNK (Cell Signaling), JNK (Santa Cruz Biotechnology) or β-actin (Sigma-Aldrich), and treated with appropriate horseradish peroxidase (HRP)-conjugated secondary antibodies to develop a color. As to data, the measurement was done for 3 wells each and mean value and standard error were determined.

6) Measurement of Apoptosis

After cell attachment, hepatocytes were incubated for 16 hours without serum. Firstly, the present extract (0.2 NU/mL) was pretreated for one hour. The cells were then treated with actinomycin D (200 ng/mL, Sigma-Aldrich) and IL-1β (2 ng/mL) or actinomycin D and TNF-α (2 ng/mL) for 16 hours more. Apoptosis was examined by using the TUNEL staining kit (Roche). TUNEL positive cells were counted in 10 power fields (×100). As to data, the measurement was done for 3 wells each and mean value and standard error were determined.

7) Measurement of Fat Accumulation

IL-1β (10 ng/mL) or palmitic acid (200 μM) was added to the primary culture hepatocytes treated with the present extract (0.01, 0.1 or 0.2 NU/mL) and fat accumulation in the hepatocytes after 24 hours was evaluated by means of staining with Oil Red O.

8) Statistic Analysis

Differences between two groups were compared using the two-tailed unpaired student t-test. Differences among multiple groups were compared using one-way ANOVA. Analysis was conducted using GraphPad Prism 4.02 (GraphPad Software). When p values were less than 0.05, that was considered to be significant. Experiments were performed at least three times and, since the similar results were obtained, the representative data were presented.

Example 3 (Test Results)

1) Measurement of Activity of NF-κB by GFP Reporter

Figure 1:
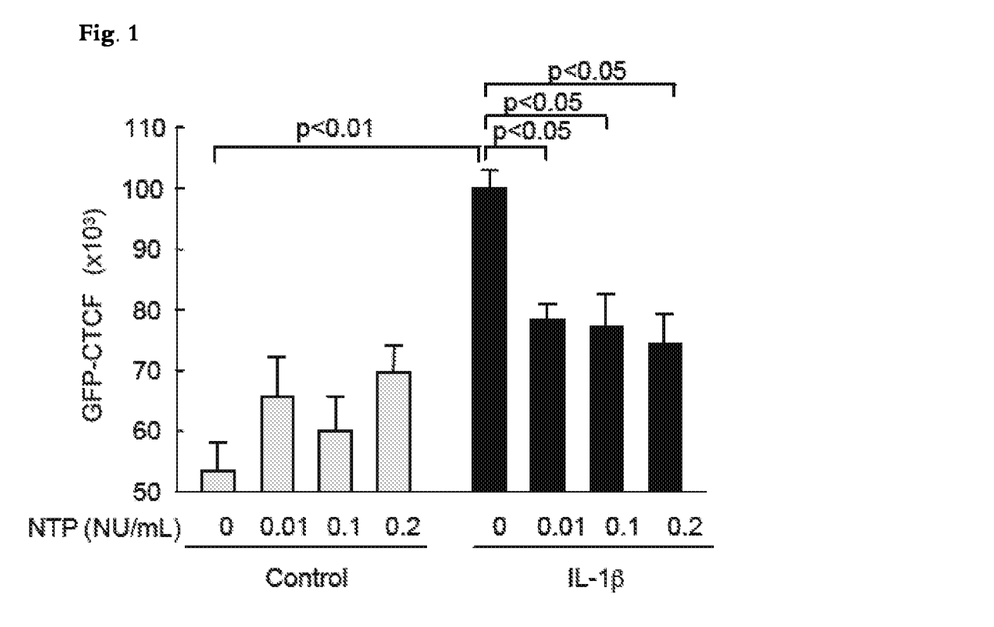
FIG. 1 is a result of the test where the inhibitory activity of the present extract for the NF-κB activation in hepatocytes was tested by a GFP reporter.

One hour before the treatment with IL-1β, a treatment with 0.01, 0.1 or 0.2 NU/mL of the present extract was conducted whereupon the NF-κB activation induced by IL-1β was significantly suppressed. An example of the results is shown in FIG. 1.

2) Measurement of Activity of NF-κB in Hepatocytes by an NF-κB Luciferase Assay

Figure 2:
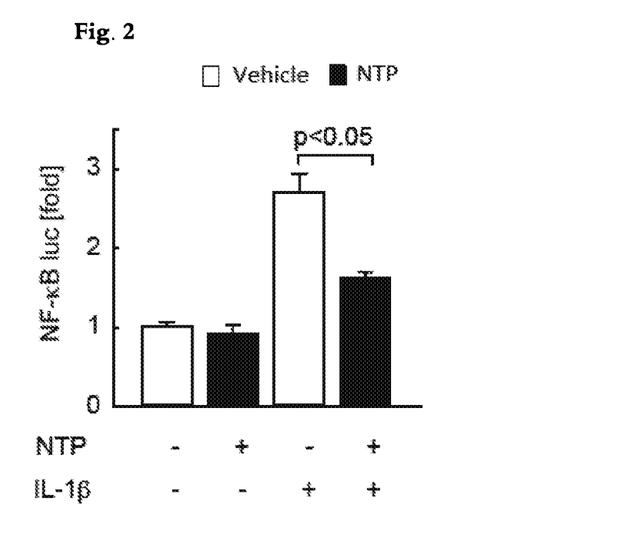
FIG. 2 is a result of the test where the inhibitory activity of the present extract for the NF-κB activation in hepatocytes was tested by an NF-κB luciferase assay.

One hour before the treatment with IL-1β, a treatment with 0.2 NU/mL of the present extract was conducted whereupon the NF-κB activation induced by IL-1β was significantly suppressed. An example of the results is shown in FIG. 2.

Figure 3A:
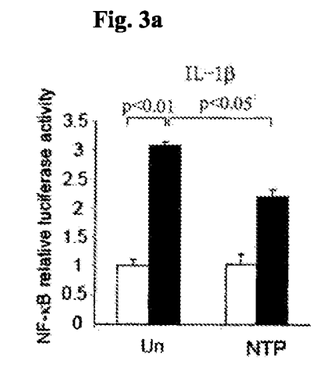
FIGS. 3a, 3b, and 3c are results of the test where the inhibitory activity of the present extract for the NF-κB activation in hepatic stellate cells was tested by an NF-κB luciferase assay.
Figure 3B:
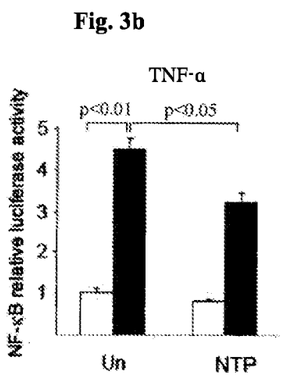
Figure 3C:
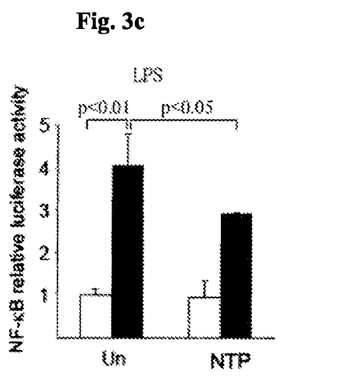
Figure 4A:
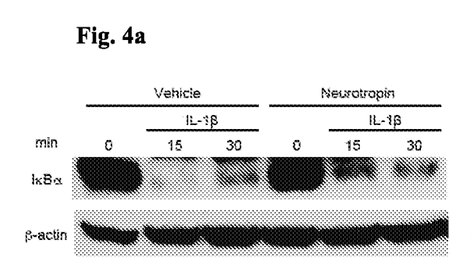
FIGS. 4a, 4b, 4c, and 4d are results of the test where the inhibitory activity of the present extract for the degradation of IκBα and the activation of p65 in hepatocytes was tested by a western blotting.
Figure 4B:
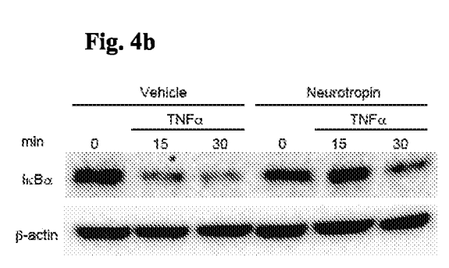
Figure 4C:
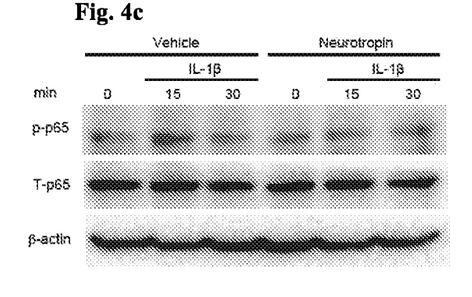
Figure 4D:
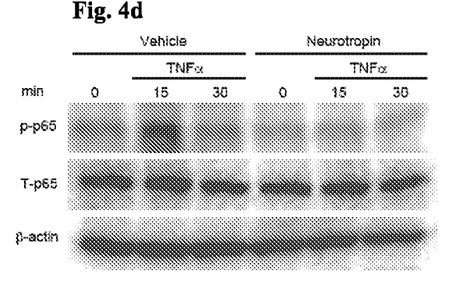
Figure 5A:
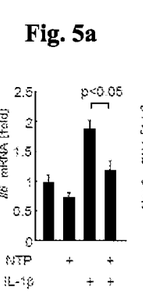
FIGS. 5a, 5b, 5c, 5d, 5e, 5f, 5g, 5h, 5i, 5j, 5k, and 5l are results of the test where the suppressive activity of the present extract for the mRNA expression and the protein expression of NF-κB target genes in hepatocytes was tested.
Figure 5B:
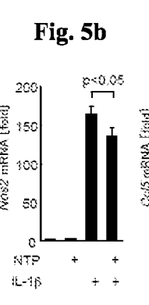
Figure 5C:
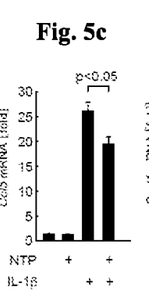
Figure 5D:
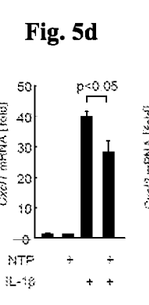
Figure 5E:
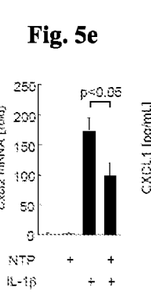
Figure 5F:
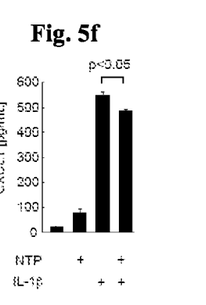
Figure 5G:
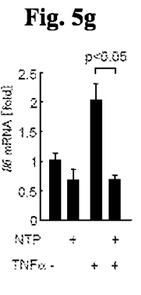
Figure 5H:
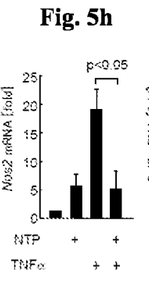
Figure 5I:
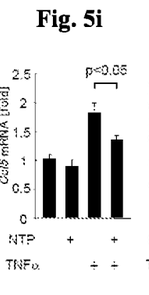
Figure 5J:
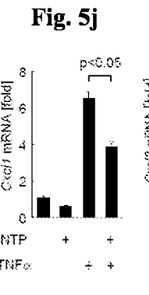
Figure 5K:
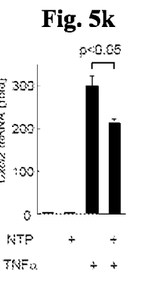
Figure 5L:
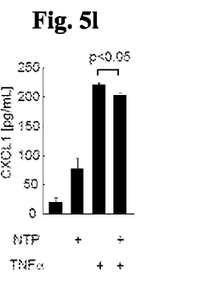

3) Measurement of Activity of NF-κB in Hepatic Stellate Cells by an NF-κB Luciferase Assay One hour before the treatment with IL-1β, TNF-α or LPS, a treatment with 0.4 NU/mL of the present extract was conducted whereupon the NF-κB activation induced by IL-1β, TNF-α or LPS in the hepatic stellate cells was significantly suppressed. An example of the results is shown in FIGS. 3a, 3b and 3c.

The suppression of NF-κB activation, particularly, in hepatic stellate cells is an effect to prevent, to treat, and to inhibit the progression of liver fibrosis.

4) Measurement of Degradation of IκBα and Activity of p65 by Western Blotting

As a result of the treatment with IL-1β or TNF-α, degradation of IκBα that inhibits nuclear translocation of NF-κB was quickly induced. As a result of the treatment with the present extract, degradation of IκBα by a treatment with IL-1β or TNF-α was delayed. Moreover, as a result of the treatment with the extract, phosphorylation of p65, a subunit of NF-κB, was attenuated. An example of the results is shown in FIGS. 4a, 4b, 4c, and 4d.

5) Measurement of Expression of NF-κB Target Genes by Quantitative Real-Time PCR and ELISA An IL-1β treatment induced an increase of expression of mRNA of IL-6, NOS2, CCL5, CXCL1 and CXCL2 and of the production of protein of CXCL1. A treatment with the present extract significantly reduced an increase of expression of mRNA of IL-6, NOS2, CCL5, CXCL1 and CXCL2 and of production of protein of CXCL1 in hepatocytes treated with IL-1β. Moreover, a TNF-α treatment induced an increase of expression of mRNA of IL-6, NOS2, CCL-5, CXCA1 and CXCL2 and of production of protein of CXCL1. Those increases were significantly suppressed by a pretreatment with the present extract. An example of the results is shown in FIGS. 5a, 5b, 5c, 5d, 5e, 5f, 5g, 5h, 5i, 5j, 5k, and 5l.

6) Measurement of JNK Activity by Western Blotting

Figure 6A:
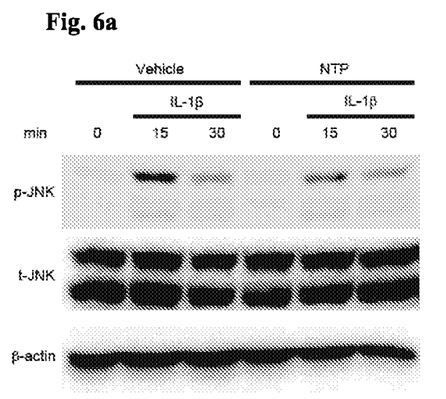
FIGS. 6a and 6b are results of the test where the inhibitory activity of the present extract for the JNK activation in hepatocytes was tested.
Figure 6B:
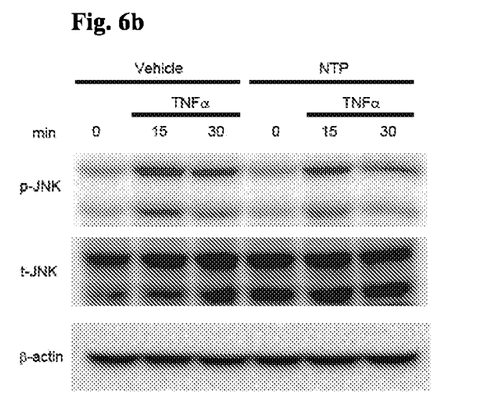

When treated with IL-1β, JNK was quickly phosphorylated in hepatocytes. JNK activation induced by IL-1β was reduced by a treatment with the present extract. Moreover, an increase of expression of Junb, a target gene of JNK, by IL-1β was significantly suppressed. Similarly, TNF-α induced a quick activation of JNK in hepatocytes and phosphorylation of JNK induced by TNF-α was suppressed by a pretreatment with the present extract. An example of the results is shown in FIGS. 6a and 6b.

7) Measurement of Apoptosis

Figure 7:
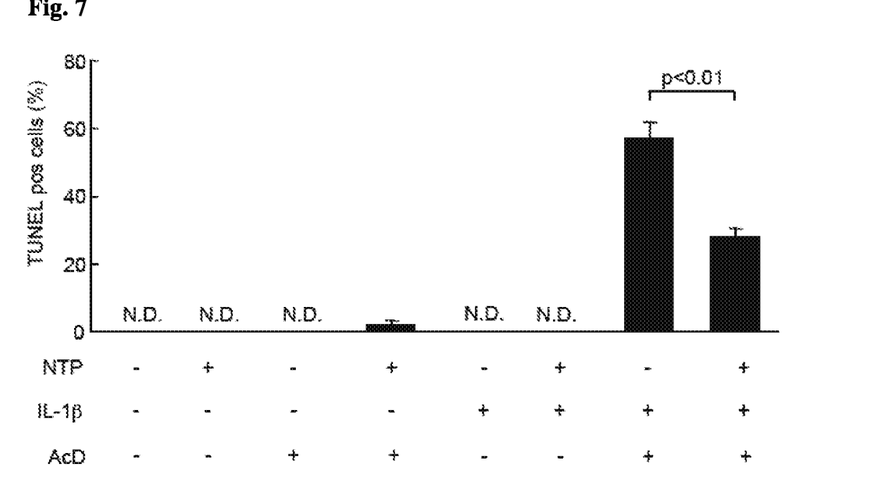
FIG. 7 is a result of the test where the inhibitory activity of the present extract for the apoptosis in hepatocytes was tested.

After 16 hours of the co-treatment with IL-1β and actinomycin D, hepatocyte apoptosis was dramatically induced. A pretreatment with the present extract reduced the apoptosis induced by co-treatment with IL-1β and actinomycin D. In addition, JNK activation related to apoptosis induced by IL-1β and actinomycin D was suppressed by a treatment with the present extract.

Similarly, after 16 hours of co-treatment with TNF-α and actinomycin D, hepatocyte apoptosis was significantly induced. A treatment with the present extract significantly reduced the hepatocyte apoptosis induced by co-treatment with TNF-α and actinomycin D. In addition, JNK activation related to the apoptosis by co-treatment with TNF-α and actinomycin D was significantly suppressed by a treatment with the present extract. An example of the results is shown in FIG. 7.

8) Measurement of Expression of Active Form of Caspase-3

Figure 8:
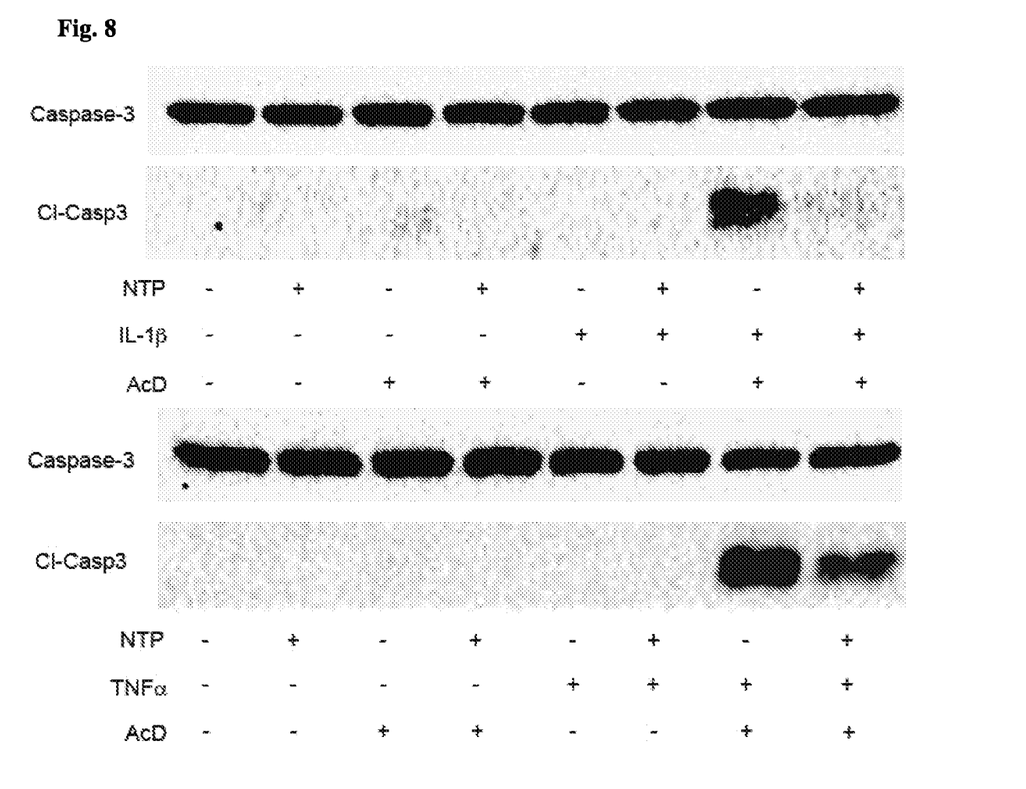
FIG. 8 is a result of the test where the inhibitory activity of the present extract for the caspase activation in hepatocytes was tested.
Figure 9A:
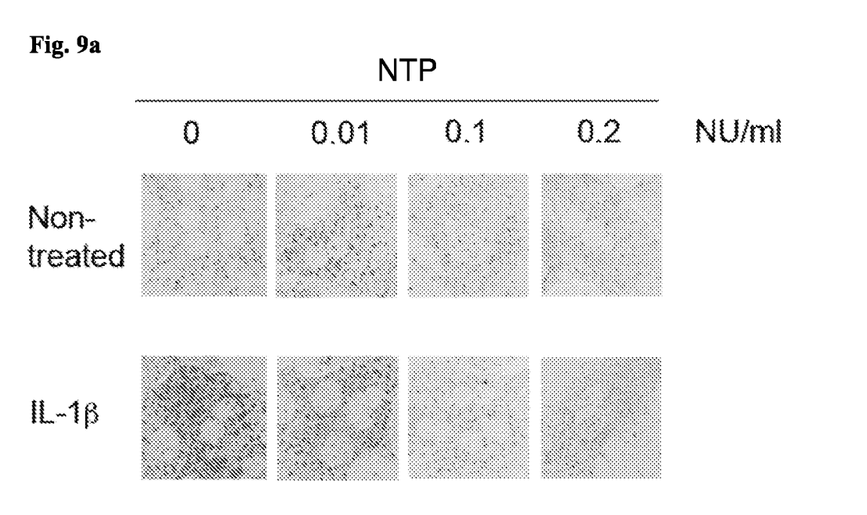
FIGS. 9a, 9b, 9c, and 9d are results of the test where the suppressive activity of the present extract for the accumulation of fat in hepatocytes was tested.
Figure 9B:
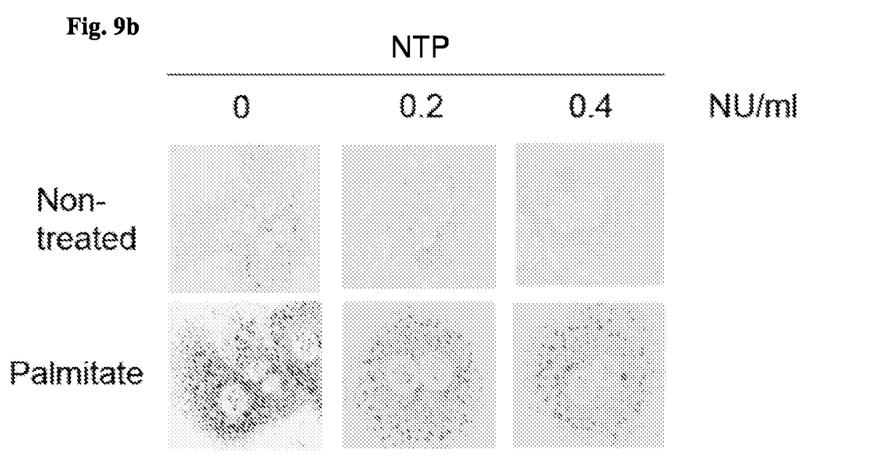
Figure 9C:
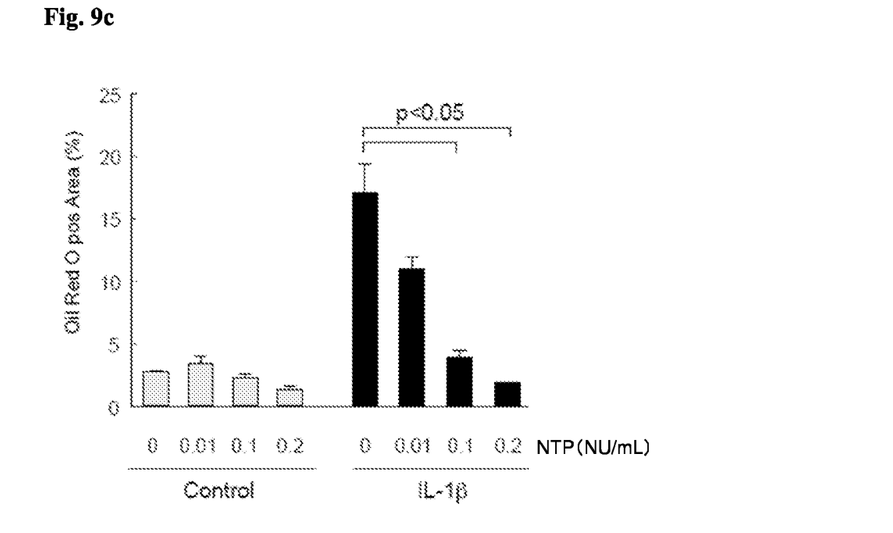
Figure 9D:
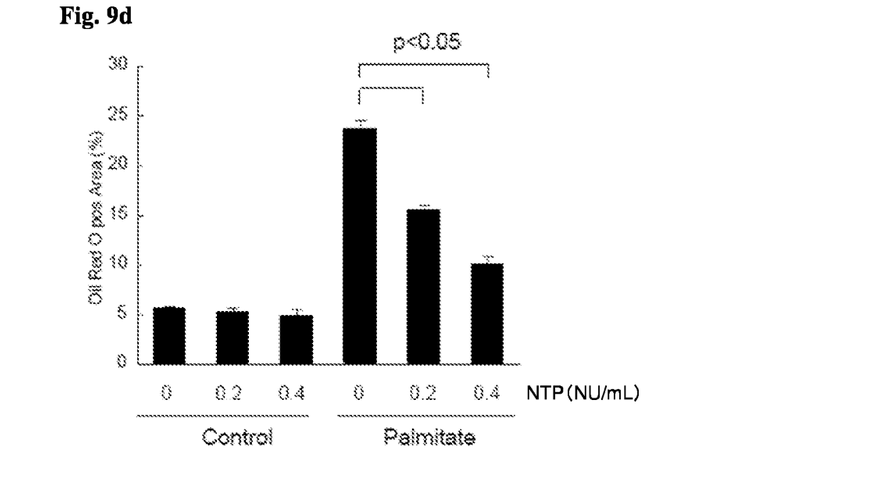

After 8 hours of co-treatment with IL-1β and actinomycin D, an increase of expression of active form of caspase-3 was observed. A pretreatment with the present extract suppressed an increase of expression of active form of caspase-3.

Similarly, after 8 hours of co-treatment with TNF-α and actinomycin D, the expression of active form of caspase-3 was increased. A treatment with the present extract suppressed an increase of expression of the active form of caspase-3. An example of the results is shown in FIG. 8.

9) Measurement of Fat Accumulation

After 24 hours of treatment with either IL-1β or palmitic acid, apparent fat accumulation in hepatocytes was confirmed. As a result of treatment with the present extract, the fat accumulation induced by IL-1β or palmitic acid was significantly suppressed. An example of the results is shown in FIGS. 9a, 9b, 9c, and 9d.

It was also demonstrated that, as a result of a treatment with the present extract, an AMP activating kinase related to the suppression of fat accumulation was activated.

In view of the above, the followings, but not limited to, can be introduced as the present invention.

(1) A method for the protection of liver comprising administration of an extract from inflamed tissues inoculated with vaccinia virus to a patient in need thereof.

(2) The method according to (1), wherein the protection of liver is by means of prevention, treatment or suppression of progress of chronic liver disease.

(3) The method according to (1), wherein the protection of liver is by means of prevention, treatment or suppression of progress of hepatic fibrosis.

(4) The method according to (3), wherein prevention, treatment or suppression of progress of hepatic fibrosis is by means of suppression of activation of hepatic stellate cells.

(5) The method according to (1), wherein the protection of liver is by means of prevention or treatment of fatty liver or suppression of progress to liver disease.

(6) The method according to any of (1) to (5), wherein the protection of liver is by means of inhibition of NF-κB activation.

(7) The method according to any of (1) to (5), wherein the protection of liver is by means of inhibition of JNK activation.

(8) The method according to any of (1) to (5), wherein the protection of liver is by means of suppression of hepatocyte apoptosis.

(9) The method according to (8), wherein the suppression of hepatocyte apoptosis is by means of inhibition of caspase activation.

(10) The method according to any of (1) to (5), wherein the protection of liver is by means of suppression of fat accumulation in liver.

(11) The method according to any of (1) to (5), wherein the extract from inflamed tissues inoculated with vaccinia virus to be administered is an extract from inflamed skins of rabbits inoculated with vaccinia virus.

(12) The method according to (11), wherein the administration is by means of injection.

(13) The method according to (11), wherein the administration is by means of oral route.

(14) A liver protecting agent containing an extract from inflamed tissues inoculated with vaccinia virus as an active ingredient.

(15) The liver protecting agent according to (14), which is a preventing, treating or progress-suppressing agent for chronic liver disease.

(16) The liver protecting agent according to (14), which is a preventing, treating or progress-suppressing agent for hepatic fibrosis.

(17) The liver protecting agent according to (16), wherein prevention, treatment or suppression of progress of hepatic fibrosis is by means of suppression of activation of hepatic stellate cells.

(18) The liver protecting agent according to (14), which is a preventive or treating agent for fatty liver or is a progress-suppressing agent to liver diseases.

(19) The liver protecting agent according to any of (14) to (18), wherein the protection of liver is by means of inhibition of NF-κB activation.

(20) The liver protecting agent according to any of (14) to (18), wherein the protection of liver is by means of inhibition of JNK activation.

(21) The liver protecting agent according to any of (14) to (18), wherein the protection of liver is by means of suppression of apoptosis.

(22) The liver protecting agent according to (21), wherein the suppression of apoptosis is by means of inhibition of caspase activation.

(23) The liver protecting agent according to any of (14) to (18), wherein the protection of liver is by means of suppression of fat accumulation in liver.

(24) The liver protecting agent according to any of (14) to (18), wherein the inflamed tissues are inflamed skins of rabbits.

(25) The liver protecting agent according to (24), which is an injectable preparation.

(26) The liver protecting agent according to (24), which is an oral preparation.

(27) An extract from inflamed tissues inoculated with vaccinia virus to be used for the protection of liver.

(28) The extract from inflamed tissues inoculated with vaccinia virus according to (27), wherein the protection of liver is by means of prevention, treatment or suppression of progress of chronic liver disease.

(29) The extract from inflamed tissues inoculated with vaccinia virus according to (27), wherein the protection of liver is by means of prevention, treatment or suppression of progress of hepatic fibrosis.

(30) The extract from inflamed tissues inoculated with vaccinia virus according to (29), wherein the prevention, treatment or suppression of progress of hepatic fibrosis is by means of suppression of activation of hepatic stellate cells.

(31) The extract from inflamed tissues inoculated with vaccinia virus according to (27), wherein the protection of liver is by means of prevention, treatment of fatty liver or suppression of progress to liver diseases.

(32) The extract from inflamed tissues inoculated with vaccinia virus according to any of (27) to (31), wherein the protection of liver is by means of inhibition of NF-κB activation.

(33) The extract from inflamed tissues inoculated with vaccinia virus according to any of (27) to (31), wherein the protection of liver is by means of inhibition of JNK activation.

(34) The extract from inflamed tissues inoculated with vaccinia virus according to any of (27) to (31), wherein the protection of liver is by means of inhibition of suppression of hepatocyte apoptosis.

(35) The extract from inflamed tissues inoculated with vaccinia virus according to (34), wherein the suppression of hepatocytes is by means of inhibition of caspase activation.

(36) The extract from inflamed tissues inoculated with vaccinia virus according to any of (27) to (31), wherein the protection of liver is by means of suppression of fat accumulation in the liver.

(37) The extract from inflamed tissues inoculated with vaccinia virus according to any of (27) to (31), wherein the inflamed tissues are inflamed skins of rabbits.

(38) The extract from inflamed tissues inoculated with vaccinia virus according to (37), wherein the administration is by means of injection.

(39) The extract from inflamed tissues inoculated with vaccinia virus according to (37), wherein the administration is by means of oral route.

(40) Use of an extract from inflamed tissues inoculated with vaccinia virus in the manufacture of a liver protecting agent.

(41) The use according to (40), wherein the liver protection is by means of prevention, treatment or suppression of progress of chronic liver disease.

(42) The use according to (40), wherein the liver protection is by means of prevention, treatment or suppression of progress of hepatic fibrosis.

(43) The use according to (42), wherein the prevention, treatment or suppression of progress of hepatic fibrosis is by means of suppression of activation of hepatic stellate cells.

(44) The use according to (40), wherein the liver protection is by means of prevention or treatment of fatty liver or suppression of progress to liver diseases.

(45) The use according to any of (40) to (44), wherein the liver protection is by means of inhibition of NF-κB activation.

(46) The use according to any of (40) to (44), wherein the liver protection is by means of inhibition of JNK activation.

(47) The use according to any of (40) to (44), wherein the liver protection is by means of suppression of hepatocyte apoptosis.

(48) The use according to (47), wherein the suppression of hepatocyte apoptosis is by means of inhibition of caspase activation.

(49) The use according to any of (40) to (44), wherein the liver protection is by means of suppression of fat accumulation in liver.

(50) The use according to any of (40) to (44), wherein the inflamed tissues are inflamed skins of rabbits.

(51) The use according to (50), wherein the administration is by means of injection.

(52) The use according to (50), wherein the administration is by means of oral route.

INDUSTRIAL APPLICABILITY

As mentioned hereinabove, it has now been made clear that the present extract exhibits an inhibitory or suppressive action to the NF-κB activation in hepatocytes induced by IL-1β or TNF-α, the expression of NF-κB target gene, the JNK activation, the hepatocyte apoptosis, etc. and a suppressive action to the fat accumulation. In view of those results, it has now been believed that administration of the present extract is able to be an effective preventive or treating method for chronic liver disease in which NF-κB or JNK is thought to be participated, for hepatic fibrosis in which activation of hepatic stellate cells is participated and/or for progress of fatty liver to liver disease. In addition, the preparation containing the present extract has been used for many years and recognized as a drug having little adverse effect and high safety whereby it is able to become a useful preventive or treating agent for chronic liver disease and/or for progress of fatty liver to liver disease. As such, the present invention is to provide a novel protective method for liver and a novel liver protecting agent whereby it is highly useful.

We claim:

1. A method for treatment of patients with chronic liver disease, fatty liver, hepatic fibrosis, or cirrhosis in need of inhibition of NF-κB activation, inhibition of JNK activation, suppression of hepatocyte apoptosis, or inhibition of caspase activation comprising testing hepatocytes or hepatic stellate cells of said patients for NF-κB activation, JNK activation, hepatocyte apoptosis, or caspase activation and administering an extract from inflamed tissues inoculated with vaccinia virus to patients to inhibit NF-κB activation, inhibit JNK activation, suppress hepatocyte apoptosis, or inhibit caspase activation in patients in need thereof.

2. The method according to claim 1, wherein the treatment inhibits NF-κB activation, inhibits JNK activation, suppresses hepatocyte apoptosis, or inhibits caspase activation in patients with chronic liver disease.

3. The method according to claim 1, wherein the treatment inhibits NF-κB activation, inhibits JNK activation, suppresses hepatocyte apoptosis, or inhibits caspase activation in patients with hepatic fibrosis.

4. The method according to claim 3, wherein hepatic stellate cells of said patients are tested for NF-κB activation, and the treatment of the patients with hepatic fibrosis comprises suppression of activation of NF-κB in hepatic stellate cells.

5. The method according to claim 1, wherein treatment inhibits NF-κB activation, inhibits JNK activation, suppresses hepatocyte apoptosis, or inhibits caspase activation in patients with fatty liver.

6. The method according to claim 1, wherein the hepatocytes or hepatic stellate cells of said patients are tested for NF-κB activation, and the treatment comprises inhibition of NF-κB activation in the patients.

7. The method according to claim 1, wherein the hepatocytes or hepatic stellate cells of said patients are tested for JNK activation, and the treatment comprises inhibition of JNK activation in the patients.

8. The method according to claim 1, wherein the hepatocytes of said patients are tested for hepatocyte apoptosis, and the treatment comprises suppression of hepatocyte apoptosis in the patients.

9. The method according to claim 8, wherein the hepatocytes of said patients are tested for caspase activation, and the treatment comprises suppression of the apoptosis by inhibition of caspase activation in the patients.

10. The method according to claim 1, wherein the hepatocytes of said patients are tested, and the treatment comprises suppression of fat accumulation in the liver of the patients.

11. The method according to claim 1, wherein the extract of inflamed tissues inoculated with vaccinia virus which is administered is an extract from inflamed skins of rabbits inoculated with vaccinia virus.

12. The method according to claim 11, wherein the administration is by injection.

13. The method according to claim 11, wherein the administration is by the oral route.

14. The method according to claim 2, wherein the hepatocytes or hepatic stellate cells of said patients are tested for NF-κB activation, and the treatment comprises inhibition of NF-κB activation.

15. The method according to claim 3, wherein the hepatocytes or hepatic stellate cells of said patients are tested for NF-κB activation, and the treatment comprises inhibition of NF-κB activation.

16. The method according to claim 4, wherein the testing for NF-κB activation is by an NF-κB luciferase assay.

17. The method according to claim 5, wherein the hepatocytes or hepatic stellate cells of said patients are tested for NF-κB activation or JNK activation, and the treatment comprises inhibition of NF-κB activation or inhibition of JNK activation.

18. The method according to claim 2, wherein the extract of inflamed tissues inoculated with vaccinia virus which is administered is an extract from inflamed skins of rabbits inoculated with vaccinia virus.

19. The method according to claim 3, wherein the extract of inflamed tissues inoculated with vaccinia virus which is administered is an extract from inflamed skins of rabbits inoculated with vaccinia virus.

20. The method according to claim 4, wherein the extract of inflamed tissues inoculated with vaccinia virus which is administered is an extract from inflamed skins of rabbits inoculated with vaccinia virus.

21. The method according to claim 1, wherein the testing of the hepatocytes or hepatic stellate cells of said patients for NF-κB activation, JNK activation, hepatocyte apoptosis, or caspase activation comprises:
   a) GFP reporter or NF-κB luciferase assay,
   b) measurement of degradation of IκBα and activity of p65 by western blotting,
   c) measurement of expression of NF-κB target genes by quantitative real-time PCR and ELISA,
   d) measurement of JNK activity by western blotting, or
   e) measurement of expression of active form of caspase-3.

* * * * *

UNITED STATES PATENT AND TRADEMARK OFFICE
CERTIFICATE OF CORRECTION

PATENT NO. : 10,780,133 B2  
APPLICATION NO. : 15/502358  
DATED : September 22, 2020  
INVENTOR(S) : Ekihiro Seki et al.

Page 1 of 1

It is certified that error appears in the above-identified patent and that said Letters Patent is hereby corrected as shown below:

On the Title Page

Item (73) Assignees, which read:
"(73) Assignees: NIPPON ZOKI PHARMACEUTICALS CO., LTD., Osaka (JP); THE REGENTS OF THE UNIVERSITY OF CALIFORNIA, Oakland CA (US)"

Should read:
-- "(73) Assignees: NIPPON ZOKI PHARMACEUTICAL CO., LTD., Osaka (JP); THE REGENTS OF THE UNIVERSITY OF CALIFORNIA, Oakland CA (US)" --

Signed and Sealed this
Eighth Day of December, 2020

Andrei Iancu
*Director of the United States Patent and Trademark Office*